United States Patent [19]

Drent

[11] 4,414,421

[45] Nov. 8, 1983

[54] PROCESS FOR THE PREPARATION OF GLYCOL ALDEHYDE

[75] Inventor: Eit Drent, Amsterdam, Netherlands

[73] Assignee: Shell Oil Company, Houston, Tex.

[21] Appl. No.: 382,029

[22] Filed: May 26, 1982

[30] Foreign Application Priority Data

Aug. 3, 1981 [GB] United Kingdom ............... 8123691

[51] Int. Cl.³ .................... C07C 45/49; C07C 45/75
[52] U.S. Cl. ................................. 568/462; 568/878
[58] Field of Search ............... 568/462, 852, 882, 878

[56] References Cited

U.S. PATENT DOCUMENTS

| | | | |
|---|---|---|---|
| 3,920,753 | 11/1975 | Yukawa et al. | 568/462 |
| 4,200,765 | 4/1980 | Goetz | 568/462 |
| 4,291,179 | 9/1981 | Goetz et al. | 568/462 |

*Primary Examiner*—Werren B. Lone

[57] ABSTRACT

A process for the preparation of glycol aldehyde, which comprises reacting formaldehyde with hydrogen and carbon monoxide, in the presence of a rhodium- and/or a cobalt-containing catalyst, sulphur dioxide, and water.

7 Claims, No Drawings

PROCESS FOR THE PREPARATION OF GLYCOL ALDEHYDE

FIELD OF THE INVENTION

This invention relates to a process for the preparation of glycol aldehyde.

BACKGROUND OF THE INVENTION

U.S. Pat. No. 3,920,753, issued Nov. 18, 1975 discloses that glycol aldehyde, which is a useful intermediate for preparation of ethylene glycol, can be prepared by the reaction of formaldehyde with carbon monoxide and hydrogen in the presence of a cobalt catalyst. U.S. Pat. No. 4,200,765 issued Apr. 29, 1980 and European Patent application No. 2908, published July 11, 1979 both disclose that this same chemical reaction can be carried out using a rhodium catalyst instead of a cobalt catalyst.

These prior art processes suffer from the disadvantage that much methanol is produced as a result of the hydrogenation of formaldehyde which proceeds as a side-reaction. In order to suppress the methanol production to a reasonable level, the prior art processes use very high pressures; in addition, they use carbon monoxide/hydrogen gas mixtures with a relatively high carbon monoxide content.

SUMMARY OF THE INVENTION

The invention provides a process for the preparation of glycol aldehyde, which comprises reacting formaldehyde with hydrogen and carbon monoxide in presence of a rhodium- and/or cobalt-contaning catalyst, sulphur dioxide, and water. The presence of sulphur dioxide and water in the reaction mixture improves the process when using either a cobalt or rhodium catalyst, in particular, the quantity of methanol formed is significantly reduced.

DESCRIPTION OF THE PREFERRED EMBODIMENTS

The catalyst used in the process according to the invention comprises rhodium and/or cobalt in any form generally used in catalytic reactions. The catalyst may for example be a salt or rhodium or cobalt with a mineral acid, for example a carboxylate having up to 20 carbon atoms, especially an alkanoate, such as an acetate. Alternatively, the metal may be in zero valent form, optionally complexed by ligands such as the phosphine ligands described below, carbon monoxide, or acetylacetonates. Frequently both anions and uncharged ligands are present, e.g. as in $[Rh.Cl(CO)_2]_2$. The precise form of the active catalyst species in the process of the invention is not known; in some cases the rhodium- or cobalt-containing species added to the reaction mixture will itself function directly as a catalyst, in others it will be converted into an active form in situ.

In general, although catalysts containing halide ions are extremely effective when used in the process according to the invention, it may be preferred to use a halide-free system since halide ions tend to be corrosive, causing problems in maintaining equipment. Thus, the use of a halide-free rhodium or cobalt catalyst may be advantageous.

The quantity of rhodium or cobalt present in the reaction mixture is generally determined by economic considerations. Quantities of rhodium plus cobalt of between about 0.001 to about 10%, especially about 0.01 to about 5%, calculated as gram atoms of metal per mole of formaldehyde used as feedstock, are generally suitable. Generally rhodium is more active as a catalyst than cobalt, but the use of cobalt may be desirable because of its relatively low cost. In certain cases, a catalyst system containing both rhodium and cobalt may be useful.

The amount of sulphur dioxide present in the reaction mixture is not critical and a catalytic quantity of sulphur dioxide is adequate to increase the selectivity of the reaction to glycol aldehyde. Suitably the maximum number of moles of sulphur dioxide added per gram atom of rhodium plus cobalt is about 100; preferably the number of moles added per gram atom of rhodium plus cobalt is within the range of from about 0.1 to about 20, especially from about 0.5 to about 10.

The formaldehyde starting material may be introduced into the reaction zone in any suitable form, and it may be generated in situ. Paraformaldehyde is a convenient source. Commercial formaldehyde often contains varying quantities of either methanol or water, depending on how the material has been synthesized, and the process according to the invention can be carried out successfully using such feedstocks. Aqueous solutions, for example, 40% aqueous formaldehyde, are readily available and provide suitable feedstocks.

The amount of water present in the reaction mixture is not critical, and the quantities of water normally found in commercial formaldehyde feedstocks are in general adequate. Preferably the number of moles of water present is at least about 0.1, preferably at least about 0.5, moles per gram atom of rhodium plus cobalt. If desired, large quantities of water may be present as a solvent or co-solvent.

The molar ratio of the carbon monoxide to hydrogen supplied to the system is not critical and may vary over a wide range, for example, from about 5:95 to about 95:5, preferably from about 30:70 to about 80:20. It is generally preferred to use a gas stream in which the molar ratio of $CO:H_2$ is at least about 1:1, since under such conditions the hydrogenation of formaldehyde to methanol is minimized. The reaction is conducted under pressure, for example at a pressure in the range of from about 5 to about 200, especially from about 25 to about 80, bars. Higher pressures may of course be used, but are generally uneconomical, and it is one of the advantages of the present invention that it enables relatively low pressures to be used. Inert gases may also be present in the gas stream, but as this leads to an increase in total pressure, it is generally undesirable. The reaction is preferably conducted at a temperature in the range of from about 30° to about 200° C., especially from about 50° to about 130° C. The use of a temperature as low as possible commensurate with the desired rate of reaction is preferred, since at higher temperatures, the glycol aldehyde product tends to polymerize.

The process according to the invention is suitably carried out in the presence of a solvent. Details of suitable solvents for reactions of this kind may be found in the prior art noted above; for example, as described in European Patent application No. 2908, solvents having multiple bonds from carbon to other atoms, for example as in nitriles or pyridine, and generally suitable. N,N-disubstituted amides have proved to be especially suitable solvents, optionally in a mixture with co-solvents, since they apparently exert a promoting effect on the reaction. As discussed above aqueous reaction media may be used.

If it is desired to extract the glycol aldehyde product from the reaction mixture using water it is convenient to use a water-immiscible compound, for example an ether such as dioxane or, especially a water-immiscible amide, as solvent. Suitable water-immiscible amides are those containing long-chain alkyl moieties. Alternatively, if a compound which is wholly or partially miscible with water is used, for example N,N-dimethylformamide, N,N-dimethylacetamide or a cyclic amide such as N-methylpyrrolidone, it may be convenient to use a water-immiscible co-solvent such as benzene. In this case, extraction by water removes the glycol aldehyde together with at least some of the amide leaving the rhodium or cobalt in solution in the hydrophobic co-solvent.

Although not essential for the process according to the invention, the use of a promoter in conjunction with the catalyst system is highly desirable. Suitable promoters commonly used in catalytic reactions are organo oxygen, nitrogen, phosphorus, arsenic and antimony compounds having a lone pair of electrons. Preferred promotors are organo nitrogen or, especially, organo phosphorus compounds. Suitable oxygen-containing promotors include compounds containing hydroxy, carbonyl, carbonyloxy or ether groups. Typical compounds of this type include carboxylic acids, especially hydroxy or alkoxy substituted acids, such as methoxyacetic acid or hydroxyacetic acid, ethers such a tetrahydrofuran, and amides, such as dimethylacetamide. Amides are of course an example of a promotor containing both nitrogen and oxygen atoms, and, as stated above, amides have proved to be especially useful solvents for the process according to the invention.

Suitable phosphorus, antimony and arsenic promotors include those of the general formula $XR'R''R'''$, in which X represents phosphorus, antimony or arsenic, and each of $R'$, $R''$ and $R'''$ independently represents an optionally substituted alkyl, cycloalkyl or aryl group, or $R'$ has this meaning and $R''$ and $R'''$ together represent an alkalene group. Optional substituents may be any moieties inert under the reaction conditions, for example halogen atoms, alkoxy groups, phenyl groups and groups of formula $XR'R''$. Preferably however $R'$ and $R''$ are hydrocarbyl groups and $R'''$ is a hydrocarbyl group or a group $CH_2XR'R''$ where $R'$ and $R''$ are hydrocarbyl groups. Preferably, any alkyl group has up to 20 carbon atoms; any cycloalkyl group has up to 7 carbon atoms; any aryl group is a phenyl group; and any alkylene group has up to 20 carbon atoms. Especially preferred promotors of this type are those in which each of $R',R''$ and $R'''$ independently represents an alkyl group or a phenyl group. For economic reasons, it is generally preferred that each of $R',R''$ and $R'''$ represents the same group. Preferably X represents a phosphorus atom. Typical phosphine promotors are trimethylphosphine, and triethylphosphine, tributylphosphine, triphenylphosphine, and $(phenyl)_2PCH_2P(phenyl)_2$. The use of triphenylphosphine is especially preferred. Suitable nitrogen-containing promotors include those of the general formula $NR'R''R'''$ where $R',R''$ and $R'''$ have the meanings given above, and also compounds in which the nitrogen atom forms part of a heterocyclic ring. Typical promotors of this type include pyrrole, pyrrolidine, pyridine, piperidine, pyrimidine, picoline and quinoline, and analogues thereof, for example alkyl-substituted analogues. The amount of promotor used is not critical. Except in those cases where the promotor or one of the promotors used is employed as a solvent, the ratio of promotor to catalyst is preferably in the range of from about 1:1 to about 20:1, especially from about 2:1 to about 10:1, calculated as moles of promoter per gram atom of rhodium plus cobalt. In an especially preferred embodiment of the process according to the invention, an amide is used as solvent or co-solvent and in addition a phosphorus-containing promotor is present.

The main use of glycol aldehyde is its conversion to ethylene glycol by catalytic hydrogenation. Under certain reaction conditions, some or all of the glycol aldehyde prepared by the process according to the invention may be hydrogenated insitu over the rhodium or cobalt catalyst to produce ethylene glycol, and the present invention should be understood to include the preparation of glycol aldehyde which is converted in situ into other products.

In general, however, reaction conditions which tend to favor the hydrogenation of glycol aldehyde immediately as it is formed, tend also to favor the hydrogenation of the formaldehyde starting material to methanol. Usually, therefore, the highest overall yields of ethylene glycol are obtained by preparing glycol aldehyde under reaction conditions which minimize hydrogenation, and subsequently hydrogenating the glycol aldehyde product in a second reaction step.

The glycol aldehyde product is rather difficult to hydrogenate in the presence of sulphur dioxide, but it is a particular advantage of the process according to the invention that the sulphur dioxide can be removed from the reaction mixture simply by reducing the pressure. The glycol aldehyde can then be hydrogenated in situ over the same rhodium or cobalt catalyst, simply by repressurising with hydrogen. If desired, an additional hydrogenation catalyst can be added directly to the reaction mixture after depressurising, in the presence of the rhodium or cobalt catalyst. Alternatively, the glycol aldehyde can be separated from the rhodium or cobalt catalyst, and hydrogenated over a different hydrogenation catalyst.

Hydrogenation catalysts are well known; for example palladium, platinum or nickel catalysts, often in heterogeneous form, are commonly used. Hydrogen gas which is free from substantial quantities of carbon monoxide is of course a preferred reactant for the hydrogenation when using a hydrogenation catalyst which is poisoned by carbon monoxide. If it is desired to work-up the reaction mixture resulting from the preparation of glycol aldehyde before the glycol aldehyde is hydrogenated, this may be carried out in known manner. For example the glycol aldehyde may be extracted using a suitable solvent. As described above, water is a convenient extractant. A further convenient extractant is ethylene glycol itself. The resulting solution may then be hydrogenated in a conventional manner.

The instant will be illustrated by the following illustration embodiments which are provided for illustration and are not to be construed as limiting the invention.

ILLUSTRATIVE EMBODIMENTS

EXAMPLE 1

A hastealloy C (Trade Mark) 300 ml magnet-driven autoclave was charged with 0.25 mols formaldehyde in the form of commercial water-containing paraformaldehyde, 50 mls of dimethylacetamide, 1 mmol Rh(acac)-

CO2) (where acac represents the acetylacetonate ligand) and 3 mmol triphenylphosphine. The autoclave was then flushed with carbon monoxide, and sulphur dioxide at 5 bars pressure was introduced for about 10 seconds. The autoclave was then pressurized to a working pressure of 60 bars with a carbon monoxide/hydrogen mixture, molar ratio 1:1. The pressure was maintained throughout the reaction by feeding in the CO/H₂ mixture as required. After 5 hours reaction time at a temperature of 85° C., the contents of the autoclave were cooled and analyzed using gas-liquid chromatography. Glycol aldehyde had been obtained in a yield of 52% calculated on input formaldehyde, and the selectivity of the reaction calculated as $$\frac{\text{moles glycol aldehyde}}{\text{moles glycol aldehyde + methanol}} \times 100\%$$

was 61%.

EXAMPLE 2

Example 1 was repeated except that exposure to sulphur dioxide was for about 30 seconds. The yield of glycol aldehyde was 61%, and the selectivity of the reaction was 77%.

EXAMPLE 3

Example 2 was repeated except that an additional 0.5 ml water was added to the reaction mixture at the start of the reaction, and the reaction time was only 3 hours. The yield of glycol aldehyde was 43%, and the selectivity of the reaction was 80%.

EXAMPLE 4 (comparison)

Example 1 was repeated except that no sulphur dioxide was charged to the autoclave. The yield of glycol aldehyde was 38%, and the selectivity of the reaction was 52%.

EXAMPLE 5

Illustration of the Hydrogenation of Glycol Aldehyde

A reaction mixture containing glycol aldehyde can be worked up in numerous different ways. This Example illustrates the hydrogenation of glycol aldehyde in various model systems whigh might have resulted from its preparation.

Run (a). 3 glycol aldehyde; 30 mls propane-1,2-diol; 1 g palladium on charcoal (5% by weight). Reaction at 80° C. for 5 hours under a hydrogen pressure of 50 bars gave a yield of 80% ethylene glycol.

Run (b). 4 glycol aldehyde; 30 mls water; 1 g nickel 1404T (Trade Mark: Harshaw) catalyst. Reaction 85° C. for 5 hours under a hydrogen pressure of 5 bars, gave a quantitative yield of ethylene glycol.

Run (c). 4 g glycol aldehyde; 24 mls water; 6 mls DMF: 1 g nickel 1404T (Trade Mark: Harshaw) catalyst. Reaction at 80° C. for 5 hours under a hydrogen pressure of 40 bars, gave a yield of 90% ethylene glycol.

Run (d). 4 g glycol aldehyde; 30 mls N-methyl-pyrrolidone; 0.5 g palladium on charcoal (5% by weight). Reaction at 110° C. for 5 hours under a hydrogen pressure of 50 bars gave a yield of 75% ethylene glycol.

I claim:

1. In a process for the preparation of glycol aldehyde, by reacting formaldehyde with hydrogen and carbon monoxide at a temperature in the range from about 30° to 200° C. and pressure in the range from about 5 to about 200 bars in the presence of a rhodium and/or a cobalt-containing catalyst, and water the improvement which comprises that sulphur dioxide, is present during said reaction.

2. The process as in claim 1, in which the number of moles of sulphur dioxide added per gram atom of rhodium plus cobalt is in the range of from 0.1 to 20 and in which the number of moles of water present is at least 0.1 moles per gram atom of rhodium plus cobalt.

3. The process in claim 1 in which the quantity of rhodium plus cobalt ranges between about 0.001 to about 10 percent calculated as gram atoms of metal per mole of formaldehyde.

4. The process as in claim 1, in which the molar ratio of carbon monoxide to hydrogen is within the range of from 30:70 to 80:20.

5. The process as in claim 1 carried out at a temperature in the range of from about 30° to 130° C.

6. The process as in claim 1 carried out in a reaction medium comprising an N,N-disubstituted amide as solvent or co-solvent.

7. The process as in claim 1, in which the reaction mixture also comprises a phosphorus-containing promotor.

* * * * *